US010047038B2

(12) United States Patent
Dentel et al.

(10) Patent No.: US 10,047,038 B2
(45) Date of Patent: Aug. 14, 2018

(54) WASTE TREATMENT PROCESS

(71) Applicant: Tate & Lyle Technology Limited, London (GB)

(72) Inventors: David A. Dentel, Spanish Fort, AL (US); Wayne N. Boutzale, Saraland, AL (US); Edward Farley, St. Charles, IL (US)

(73) Assignee: Tate & Lyle Technology Limited, London (GB)

( * ) Notice: Subject to any disclaimer, the term of this patent is extended or adjusted under 35 U.S.C. 154(b) by 7 days.

(21) Appl. No.: 15/039,229

(22) PCT Filed: Nov. 27, 2014

(86) PCT No.: PCT/GB2014/053520
§ 371 (c)(1),
(2) Date: May 25, 2016

(87) PCT Pub. No.: WO2015/079239
PCT Pub. Date: Jun. 4, 2015

(65) Prior Publication Data
US 2017/0158615 A1  Jun. 8, 2017

Related U.S. Application Data

(60) Provisional application No. 61/909,449, filed on Nov. 27, 2013.

(51) Int. Cl.
*C07C 231/10* (2006.01)
*C02F 1/02* (2006.01)
(Continued)

(52) U.S. Cl.
CPC ............ *C07C 231/10* (2013.01); *C02F 1/025* (2013.01); *C02F 1/66* (2013.01); *C07C 209/84* (2013.01);
(Continued)

(58) Field of Classification Search
None
See application file for complete search history.

(56) References Cited

U.S. PATENT DOCUMENTS 2,866,822 A   12/1958  Sieffen
3,647,640 A    3/1972  Matsuzawa
(Continued)

FOREIGN PATENT DOCUMENTS

DE   3620980   1/1988
GB    690131   4/1953
(Continued)

OTHER PUBLICATIONS

"Dimethylacetamide", Kirk-Othmer Encyclopedia of Chemical Technology, Jul. 19, 2002 pp. 1-6.
Hutchinson et al., "Stability and Degradation of the High-intensity Sweeteners: Aspartame, Alitame and Sucralose", Food Reviews International, New York, vol. 15, No. 2, Jan. 1, 1999, pp. 249-261.
International Search Report and Written Opinion issued in related International Application No. PCT/GB2014/053520, dated Jun. 25, 2015.
Combined Search Report and Examination Report for GB Application No. 1321099.2, dated May 29, 2014.

*Primary Examiner* — Clinton A Brooks
*Assistant Examiner* — Jennifer C Sawyer
(74) *Attorney, Agent, or Firm* — RatnerPrestia

(57) ABSTRACT

A waste treatment process and system is described, which finds application in dechlorinating carbohydrates and/or hydrolyzing dimethyl formamide and/or dimethyl formamide in a waste stream. The process includes treating the waste stream with base at a pH of from 11 to 14, and at a temperature of from 200 to 330° F.

19 Claims, 4 Drawing Sheets

(51) Int. Cl.

| | | |
|---|---|---|
| *C02F 1/66* | (2006.01) | |
| *C07C 209/84* | (2006.01) | |
| *C02F 1/04* | (2006.01) | |
| *C02F 1/10* | (2006.01) | |
| *C02F 101/34* | (2006.01) | |
| *C02F 101/36* | (2006.01) | |
| *C02F 101/38* | (2006.01) | |
| *C02F 103/36* | (2006.01) | |

(52) U.S. Cl.
CPC ................ *C02F 1/048* (2013.01); *C02F 1/10* (2013.01); *C02F 2101/34* (2013.01); *C02F 2101/36* (2013.01); *C02F 2101/38* (2013.01); *C02F 2103/36* (2013.01); *C02F 2209/02* (2013.01); *C02F 2209/03* (2013.01); *C02F 2209/06* (2013.01)

(56) References Cited

U.S. PATENT DOCUMENTS

| 5,137,831 A | 8/1992 | Gruteser |
|---|---|---|
| 2009/0234113 A1 | 9/2009 | Liu |

FOREIGN PATENT DOCUMENTS

| JP | 2001054786 | 2/2001 |
|---|---|---|
| WO | 2005090376 | 9/2005 |
| WO | 2009146052 | 12/2009 |
| WO | 2010151489 | 12/2010 |
| WO | 2011045565 | 4/2011 |
| WO | 2011045566 | 4/2011 |

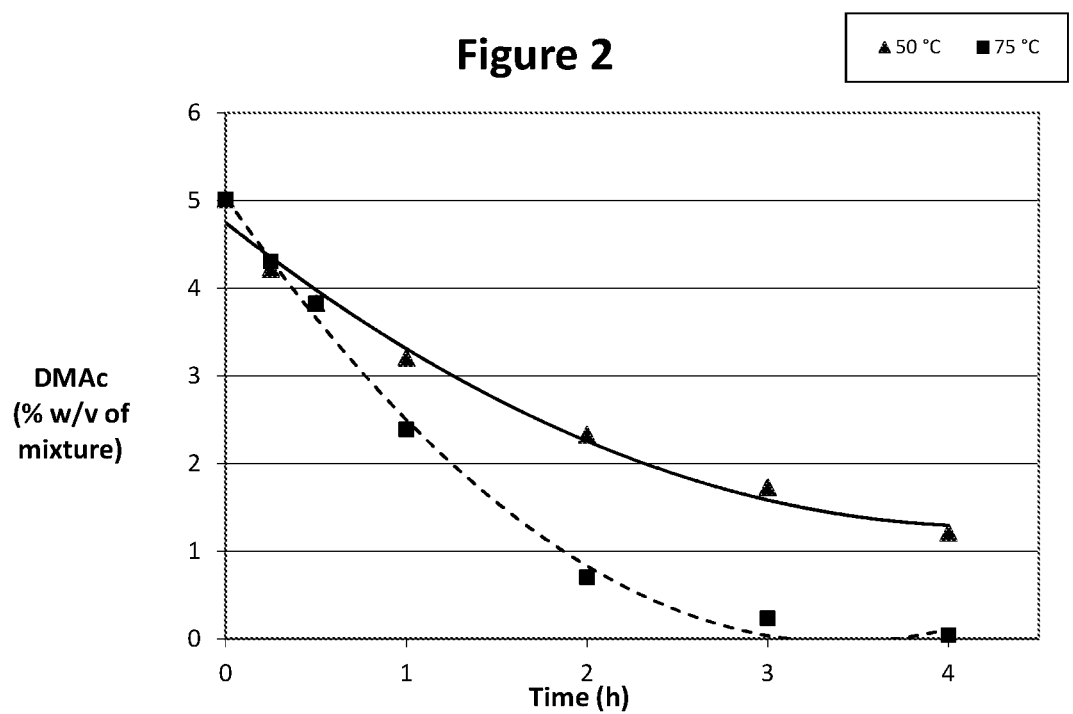
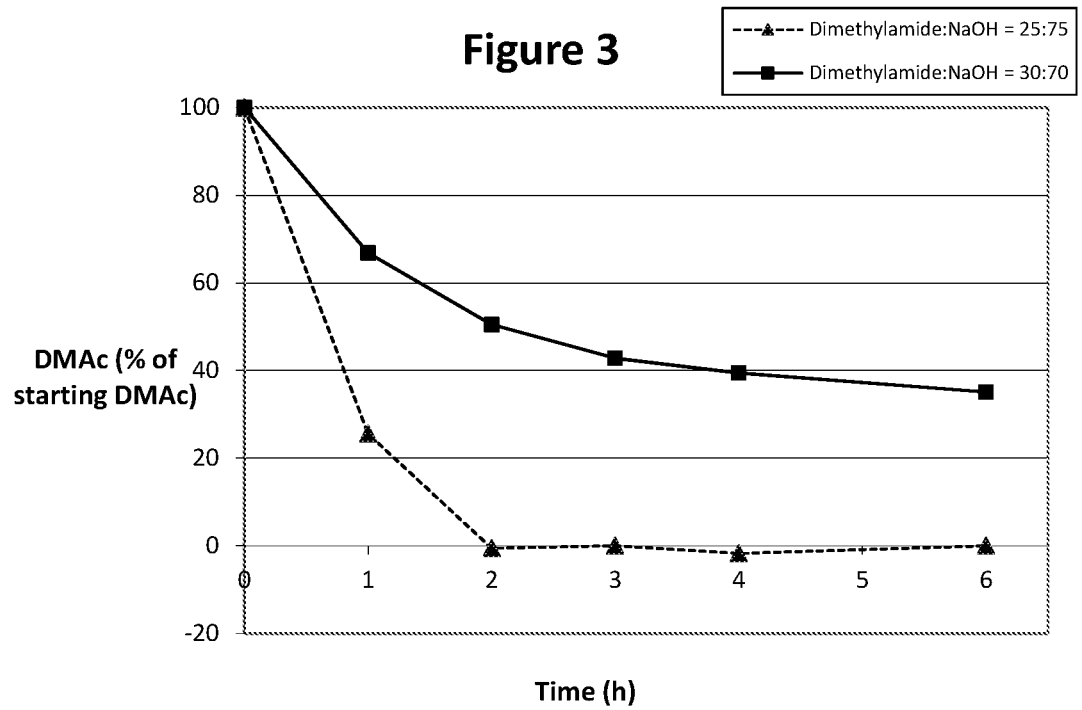

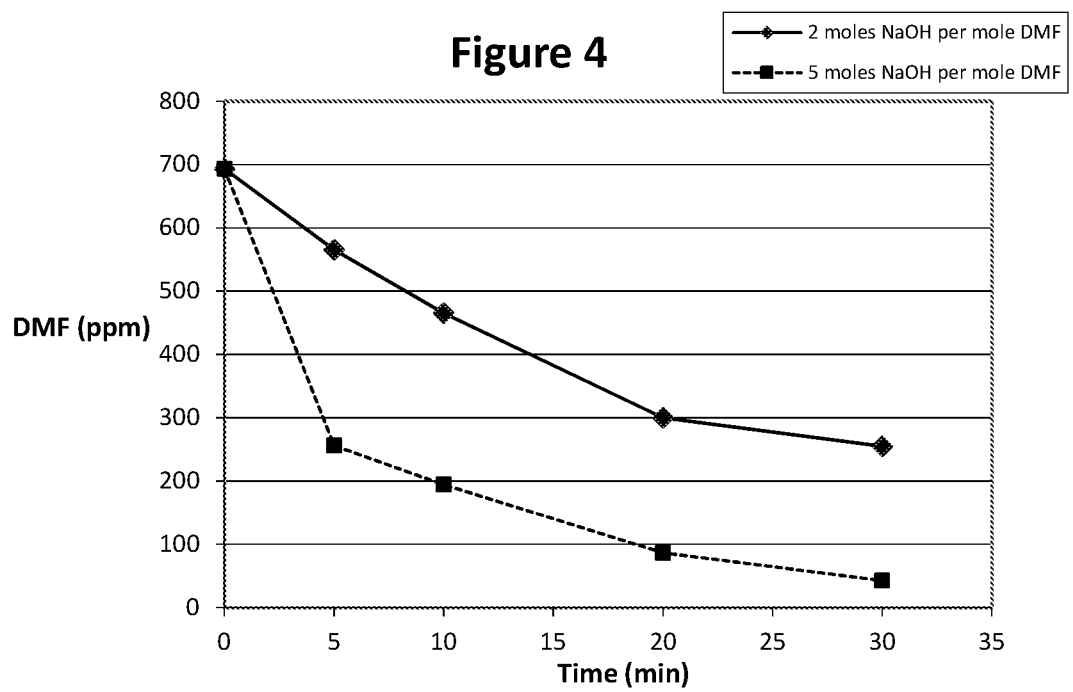
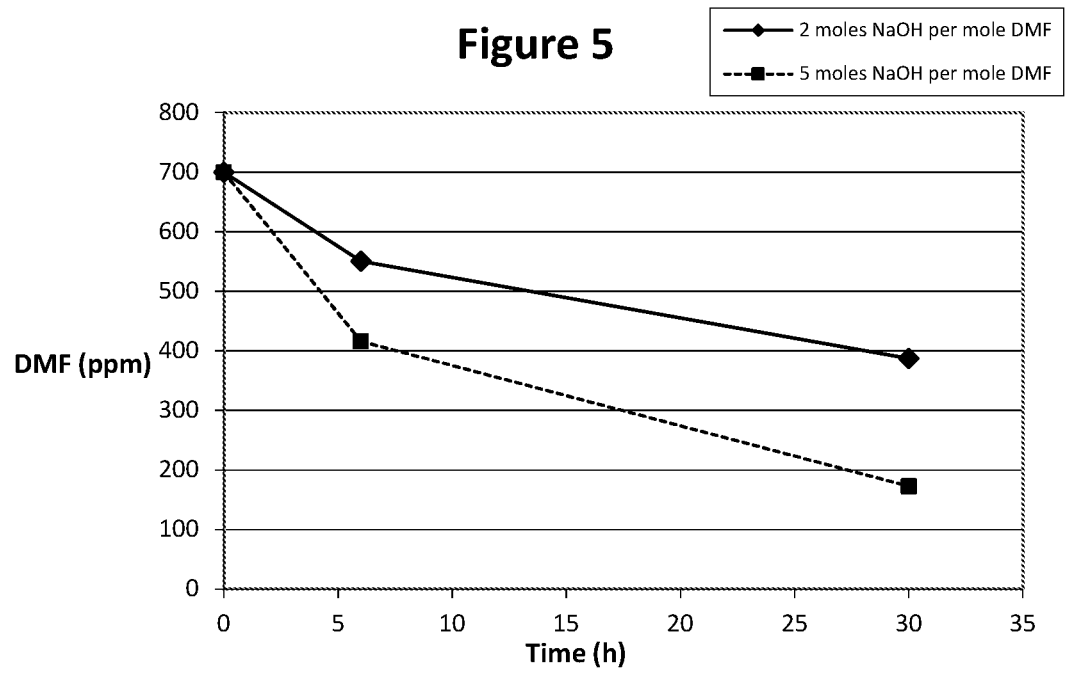

WASTE TREATMENT PROCESS

CROSS-REFERENCE TO RELATED APPLICATIONS

This is the national phase of International Application No. PCT/GB2014/053520, filed 27 Nov. 2014, which claims priority from U.S. Provisional Application No. 61/909,449, filed 27 Nov. 2013, respectively. The disclosure of each of these applications is incorporated herein by reference in its entirety for all purposes.

FIELD OF THE INVENTION

The present invention relates to a waste treatment system for a waster stream.

SUMMARY OF THE INVENTION

The waste treatment system as described herein may enable solvent recovery from the waste stream. Furthermore, the waste treatment system as described herein may improve the biodegradability of this waste stream by any subsequent biological waste treatment system. The treatment reduces the content of organic compounds in the waste stream, and thus may render it more amenable to further processing. Moreover, the chemical oxygen demand (COD) of the waste stream may be reduced by the treatment described herein.

The invention is as defined in the attached claims and the following numbered clauses. Thus, according to the invention, there is provided:

1. A method of treating a waste stream, wherein the waste stream includes at least one of chlorinated carbohydrate, dimethyl formamide and dimethyl acetamide, wherein the method comprises:
   treating the waste stream with base at a pH of from 11 to 14, and at a temperature of from 200 to 330° F.,
   in order to achieve at least one of dechlorination of said chlorinated carbohydrate, hydrolysis of said dimethyl formamide to give dimethylamine, and hydrolysis of said dimethyl acetamide to give dimethylamine.
2. A method according to clause 1, wherein the waste stream includes said chlorinated carbohydrate and the treatment achieves dechlorination of the chlorinated carbohydrate.
3. A method according to clause 1, where the waste stream includes said dimethyl formamide and the treatment achieves hydrolysis of the dimethyl formamide to give dimethylamine.
4. A method according to clause 1, where the waste stream includes said dimethyl acetamide and the treatment achieves hydrolysis of the dimethyl acetamide to give dimethylamine.
5. A method according to clause 1, wherein the waste stream includes said chlorinated carbohydrate, said dimethyl formamide and said dimethyl acetamide and the treatment achieves dechlorination of the chlorinated carbohydrate, hydrolysis of the dimethyl formamide to give dimethylamine, and hydrolysis of the dimethyl acetamide to give dimethylamine.
6. A method according to clause 1, wherein the waste stream is from a sucralose production process.
7. A method according to clause 1, wherein the waste stream includes sodium chloride, for example 5 to 20 wt % sodium chloride.
8. A method according to clause 1 wherein the base is aqueous alkali solution.
9. A method according to clause 8, wherein the base is aqueous sodium hydroxide solution, potassium hydroxide solution, or aqueous ammonia.
10. A method according to clause 9, wherein the base is aqueous sodium hydroxide solution.
11. A method according to clause 10, wherein the base is from 10 to 50% w/w sodium hydroxide solution.
12. A method according to clause 11, wherein the base is from 23 to 32% w/w sodium hydroxide solution.
13. A method according to clause 1, wherein the pH of the treatment is from 11 to 13.5.
14. A method according to clause 13, wherein said pH is from 12 to 13.
15. A method according to clause 1, wherein the temperature of the treatment is from 210 to 280° F., for example at 215 to 220° F., at 240 to 250° F., at 250 to 260° F., or at 260 to 270° F.
16. A method according to clause 1, wherein the pressure of the treatment is from 20 to 75 psig, for example from 25 to 35 psig or from 30 to 35 psig.
17. A method according to clause 1, wherein the waste stream is in aqueous medium, or in aqueous solution.
18. A method according to any of clauses 3 to 5, wherein dimethylamine is recovered from the treatment.
19. A method according to clause 18, wherein the dimethylamine is recovered by distillation.
20. A method according to clause 19, wherein the dimethylamine is converted into dimethylformamide.
21. A method according to clause 1, wherein the treatment achieves dechlorination of said chlorinated carbohydrate, and at least one of
   hydrolysis of said dimethyl formamide to give dimethylamine, and
   hydrolysis of said dimethyl acetamide to give dimethylamine.

In other words, in the embodiment of clause 21, the treatment process dechlorinates chlorinated carbohydrates and hydrolyses one or both of dimethyl formamide and dimethyl acetamide.

22. A method according to any preceding clause, wherein the treated stream is discharged after treatment.

As used in the claims, the above numbered clauses and herein, by "the treatment achieves dechlorination" it is meant that some dechlorination occurs, that is, some chloride is liberated from chlorinated carbohydrate that is present. For example, at least 50%, or at least 70%, or at least 90% of the chlorine present in the chlorinated carbohydrate may be liberated as chloride.

As used in the claims, the above numbered clauses and herein, by "the treatment achieves hydrolysis" is meant that some hydrolysis occurs, that is, some dimethyl formamide and/or dimethyl acetamide that is present is hydrolysed to afford dimethylamine. For example, at least 50%, or at least 70%, or at least 90% of dimethyl formamide that is present in the waste stream may be hydrolysed to afford dimethylamine, and/or at least 50%, or at least 70%, or at least 90% of dimethyl acetamide that is present in the waste stream may be hydrolysed to afford dimethylamine.

A specific embodiment of a waste treatment system is as follows. The system is described by reference to particular features, but these are not intended to limit the invention or its scope, which is as set out in the subsequent claims.

All documents mentioned herein are expressly incorporated by reference in their entirety.

BRIEF DESCRIPTION OF THE DRAWINGS

FIG. 2 is a graph which shows the rate of hydrolysis of dimethylacetamide (DMAc) in an aqueous solution of DMAc and NaOH at 50° C. and 75° C.

FIG. 3 is a graph which shows the rate of hydrolysis of DMAc in an aqueous solution of DMAc, dimethylformamide (DMF) (DMAc:DMF=1:9 w/w) and NaOH at 90° C.

FIG. 4 is a graph which shows the rate of hydrolysis of DMF in an aqueous solution of DMF and NaOH at 103° C. (starting DMF concentration=700 ppm)

FIG. 5 is a graph which shows the rate of hydrolysis of DMF in an aqueous solution of DMF and NaOH at 25° C. (starting DMF concentration=700 ppm).

DETAILED DESCRIPTION OF CERTAIN EMBODIMENTS OF THE INVENTION

Figure 1:
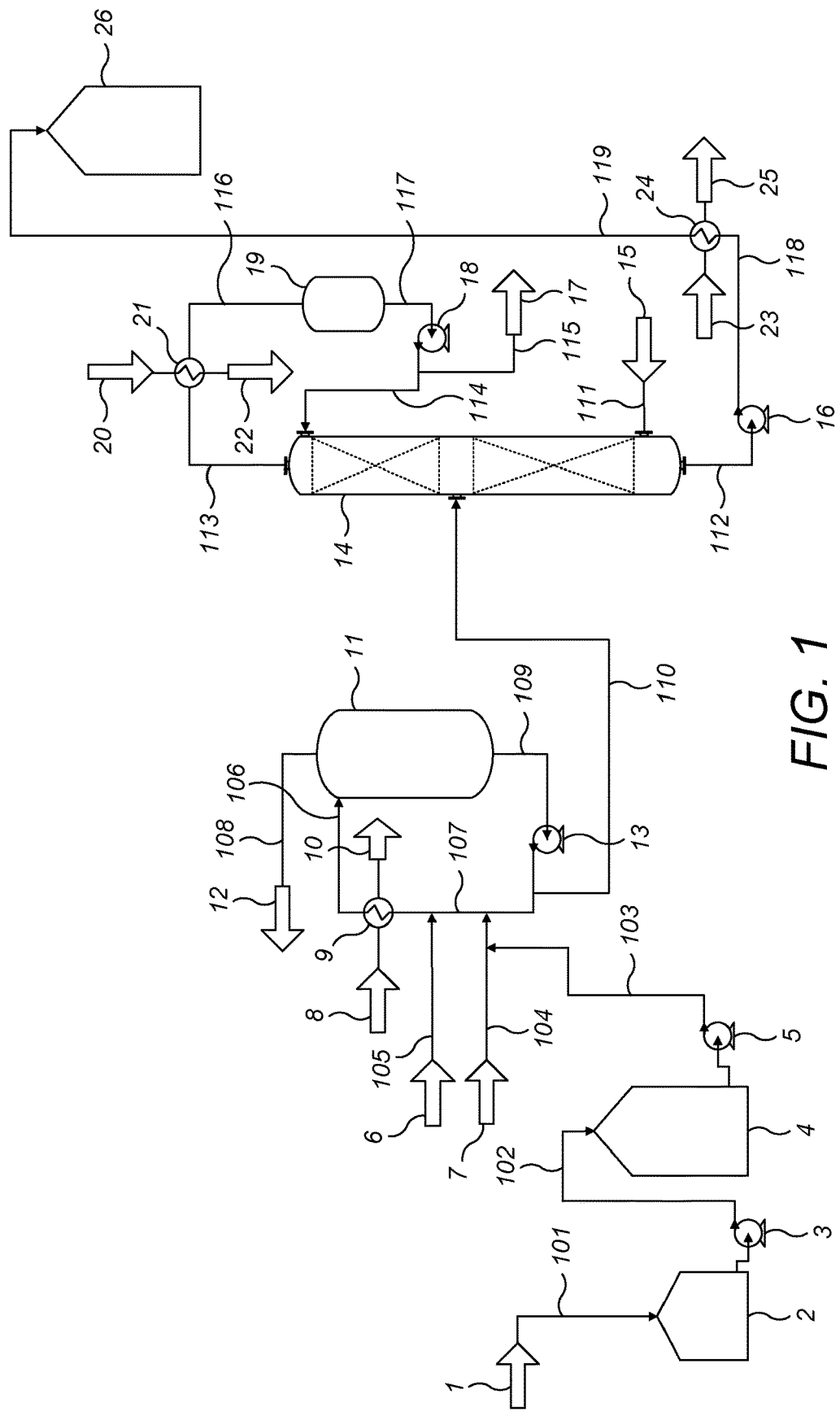
FIG. 1 is a process flow diagram illustrating a waste treatment process.

Referring to the FIG. 1, there is provided a waste treatment system. The system will now be further described in relation to treatment of waste from a sucralose production process. However, as will be clear to those skilled in the art, the process of the present invention can be applied to any waste stream that includes one or more of chlorinated carbohydrate, dimethyl formamide and dimethyl acetamide.

The input stream 1 for the waste treatment system may derive from various waste streams from a sucralose production process.

The sources of waste stream can include, for example:
A waste stream from a sucralose purification process such as is disclosed in WO 2009/146052.
Dimethyl acetamide obtained from purification of dimethyl formamide, such as is disclosed in WO 2010/151489.
Sodium acetate—containing waste from the acetylation of sucrose, such as is disclosed in WO 2011/045565 and WO/2011/045566, and prior processes referred to therein.
Other waste streams from sucralose production processes, including acetylation, chlorination, and deacetylation reactions.

The individual sources of waste may not be in aqueous medium, but generally the combined stream will be in aqueous medium, and conveniently in aqueous solution.

The feed into the waste treatment reactor, combined from one or more sources, may contain in an aqueous medium one or more of the following:
Sodium chloride in an amount of 5 to 20% w/w
Sodium acetate in an amount of 1 to 3% w/w
Sodium formate in an amount of 1 to 3% w/w
Dimethyl formamide in an amount of 1 to 3% w/w
Dimethyl acetamide in an amount of 1 to 3% w/w
Dimethylamine and/or dimethylamine hydrochloride in a total amount of 5 to 10% w/w.

One or more of these waste streams can be combined into a single feed stream 101 which passes to holding tank 2. This then passes via pump 3 becoming stream 102 to feed tank 4, and then via pump 5 to become stream 103 which is fed, for example via streams 107 and 106, into reactor 11, the destruction reactor wherein the main waste treatment step occurs. Namely, in reactor 11, dechlorination of chlorinated carbohydrate and/or hydrolysis of dimethyl formamide and/ or dimethyl acetamide takes place. In some embodiments, in reactor 11, dechlorination of chlorinated carbohydrate and hydrolysis of (a) dimethyl formamide and/or (b) dimethyl acetamide takes place. One or more further waste streams 7 can be added if desired at this point as shown as feed stream 104, for example by feeding into stream 107. These may be from a different waste stream from those combined to give input stream 1, or may be further material from one of the same streams. Caustic (aqueous sodium hydroxide solution) 6 is added as feed stream 105, for example by feeding into stream 107. Alternatively to caustic, another base, or aqueous alkali solution, such as aqueous sodium hydroxide solution, potassium hydroxide solution, or aqueous ammonia, can be employed. The caustic can be 23-32% w/w, for example 23% w/w.

Reaction temperature in reactor 11 is controlled by the addition of low pressure steam 8 to reactor heater 9 (resulting in condensate 10). The reaction pressure in reactor 11 is controlled by the vent to the DMA scrubber 12, shown as stream 108. The reaction pressure is conveniently controlled to be slightly above the pressure of the mixture at the chosen temperature. When the reaction temperature is in the range of from 200 to 330° F., the reaction pressure will typically be in the range of from 20 to 75 psig. When the reaction temperature is in the range of from 250 to 260° F., the reaction pressure will typically be in the range of from 30 to 35 psig. A lower temperature will result in a lower pressure, and a higher temperature will result in a higher pressure. Other exemplary conditions are at a temperature of 215 to 220° F. and a pressure of 25 to 30 psig, or a temperature of approximately 270° F. and a pressure of approximately 25 psig. The pH of the reaction can be, for example, from 11 to 14, or from 11 to 13.5, or from 12 to 13. The reaction time can be, for example, from 1 to 4 hours, typically from 2 to 3 hours, or from 140 to 150 minutes. The reaction time is determined by the pH and temperature—a lower pH or temperature will result in a longer reaction time, and a higher pH or temperature will result in a shorter reaction time.

The reaction mixture is circulated via stream 109 and pump 13, to become stream 107, and passes through reaction heater 9, being fed back into reactor 11 as stream 106. An output stream 110 is taken from stream 107, prior to the addition of streams 103, 105, and, where present, 104, to be fed into DMA distillation column 14. High pressure steam 15 is fed in as stream 111. The more volatile output stream 113 passes via condenser 21 (with cooling water input 20 and return water output 22) as stream 116 into reflux drum 19. Exiting as stream 117 via pump 18, stream 115 is the output dimethylamine solution 17. This may typically be a solution of 20-40% dimethylamine in water, for example a 30% aqueous solution of dimethylamine. Recycle stream 114 passes back into the column 14. The less volatile output stream 112 passes through pump 16 becoming stream 118 via cooler 24 (with cooling water input 23 and return water output 25) to be collected in waste storage tank 26 (which may be a plurality of tanks, eg 2 or three tanks). From there, the waste can be neutralised, as required, for example by treatment with HCl, and then the waste stream may be discharged or may pass to waste treatment.

The recovered dimethylamine can be formulated to give dimethyl formamide by known methods, and the resulting dimethyl formamide can then be used as a solvent in a sucralose production process. For example, the aqueous dimethylamine solution which is obtained from the above process can be dehydrated, and then subjected to catalytic formulation using, for example, methods disclosed in GB 690131 and U.S. Pat. No. 2,866,822. In other embodiments, the dimethylamine output stream can be discharged.

Example 1

"TOX" refers to total organic halide content, in this case total organic chloride. The molar ratio of total organic chloride to sucralose is 3:1, as a sucralose molecule contains 3 chlorine atoms.

Sucralose was dissolved in water, and the solution added to a pre-heated aqueous solution of NaOH to afford an aqueous reaction mixture comprising 2.1% w/w sucralose and either 1, 2 or 3% w/w NaOH as indicated in Table 1 (corresponding to a TOX to NaOH molar ratio of 1:1.6, 1:3.2 or 1:4.8 respectively). The mixture was heated to 103° C. under atmospheric pressure for the time indicated in Table 1, and subsequently cooled and quenched with a 45% w/w aqueous solution of citric acid (citric acid solution:reaction mixture w/w as indicated in Table 1 as "quench ratio"). The concentration of ionic chloride was measured via Cation Ion Chromatography, and is expressed in Table 1 as a percentage of the total organic chloride (TOX) present at the start of the reaction.

TABLE 1

| | Ionic chloride (as % of starting TOX) | | |
|---|---|---|---|
| Time/mins | 1% NaOH solution (quench ratio = 4:100) | 2% NaOH solution (quench ratio = 7.5:100) | 3% NaOH solution (quench ratio = 11:100) |
| 0 | 0% | 0% | 0% |
| 30 | 94% | 100% | 100% |
| 60 | 97% | 100% | 100% |
| 120 | 100% | 100% | 100% |

Example 2

Sucralose was dissolved in water, and the solution added to an aqueous solution of NaOH to afford an aqueous reaction mixture comprising 2.1% w/w sucralose and either 1, 2 or 3% w/w NaOH as indicated in Table 2 (corresponding to a TOX to NaOH molar ratio of 1:1.6, 1:3.2 or 1:4.8 respectively). The mixture was left at room temperature under atmospheric pressure for 22 h, and subsequently quenched with a 45% w/w aqueous solution of citric acid (citric acid solution:reaction mixture w/w as indicated in Table 2 as "quench ratio"). The concentration of ionic chloride was subsequently measured via Cation Ion Chromatography, and the concentrations of sucralose and 3',6'-anhydro-4,1'-dichloro-4,1'-dideoxy-galacto-sucralose via HPLC. The amount of ionic chloride measured is expressed in Table 2 as a percentage of the total organic chloride (TOX) present at the start of the reaction. The amounts of sucralose and 3',6'-anhydro-4,1'-dichloro-4,1'-dideoxy-galacto-sucralose (referred to as "Mono-anhydro sucralose" in Table 2) measured are expressed in Table 2 as percentages of the starting amount of sucralose.

TABLE 2

| NaOH concentration | Quench ratio | Ionic chloride | Sucralose | Mono-anhydro sucralose |
|---|---|---|---|---|
| 1% | 4:100 | 25% | 57% | 36% |
| 2% | 7.5:100 | 37% | 14% | 77% |
| 3% | 11:100 | 43% | 7% | 84% |

Example 3

Sucralose was dissolved in water, and the solution added to a pre-heated aqueous solution of NaOH to afford an aqueous reaction mixture comprising 2.1% w/w sucralose and 2% w/w NaOH (corresponding to a TOX to NaOH molar ratio of 1:3.2). The mixture was heated to 103° C. under atmospheric pressure for the time indicated in Table 3, and subsequently cooled and quenched with a 45% w/w aqueous solution of citric acid (citric acid solution:reaction mixture=7.5:100 w/w). The concentration of ionic chloride was subsequently measured via Cation Ion Chromatography, and the concentrations of sucralose and 3',6'-anhydro-4,1'-dichloro-4,1'-dideoxy-galacto-sucralose via HPLC. The amount of ionic chloride measured is expressed in Table 3 as a percentage of the total organic chloride (TOX) present at the start of the reaction. The amounts of sucralose and 3',6'-anhydro-4,1'-dichloro-4,1'-dideoxy-galacto-sucralose (referred to as "Mono-anhydro sucralose" in Table 3) measured are expressed in Table 3 as percentages of the starting amount of sucralose.

TABLE 3

| Time/mins | Ionic chloride | Sucralose | Mono-anhydro sucralose |
|---|---|---|---|
| 0 | 0% | 100% | 0% |
| 5 | 99% | 0% | 0% |
| 10 | 95% | 0% | 0% |
| 20 | 100% | 0% | 0% |
| 30 | 100% | 0% | 0% |

Example 4

A 10% w/w aqueous solution of dimethylacetamide (DMAc) was mixed with an equal volume of 10% w/w aqueous NaOH solution, resulting in a mixture comprising 5% w/w DMAc and 5% w/w NaOH, which was subsequently heated to 50° C. under atmospheric pressure. Aliquots were removed from the reaction mixture at the time intervals indicated in Table 4 and analysed via Cation Ion Chromatography to measure the amount of acetic acid present in the mixture. The moles of acetic acid formed were taken to directly correspond to the moles of DMAc hydrolysed.

TABLE 4

| Time/h | Acetic acid in mixture/ppm | % w/v Acetic acid in mixture | % w/v DMAc in mixture | % of DMAc hydrolysed |
|---|---|---|---|---|
| 0 | 0 | 0.00 | 5.01 | 0.0 |
| 0.25 | 5445 | 0.54 | 4.22 | 15.8 |
| 0.5 | 8135 | 0.81 | 3.83 | 23.6 |
| 1 | 12469 | 1.25 | 3.20 | 36.1 |
| 2 | 18506 | 1.85 | 2.32 | 53.6 |
| 3 | 22625 | 2.26 | 1.73 | 65.5 |
| 4 | 26203 | 2.62 | 1.21 | 75.9 |

Example 5

The experiment of Example 4 was repeated at 75° C.

TABLE 5

| Time/h | Acetic acid in mixture/ppm | % w/v Acetic acid in mixture | % w/v DMAc in mixture | % of DMAc hydrolysed |
|---|---|---|---|---|
| 0 | 0 | 0.00 | 5.01 | 0.0 |
| 0.25 | 4864 | 0.49 | 4.31 | 14.1 |
| 0.5 | 8154 | 0.82 | 3.83 | 23.6 |
| 1 | 18067 | 1.81 | 2.39 | 52.3 |
| 2 | 29700 | 2.97 | 0.70 | 86.0 |
| 3 | 32917 | 3.29 | 0.23 | 95.4 |
| 4 | 34239 | 3.42 | 0.04 | 99.2 |

The data of Examples 4 and 5 are expressed in FIG. 2.

Example 6

The term "Dimethylamide" herein refers to a mixture of 90% DMF (dimethylformamide) and 10% DMAc (dimethylacetamide) w/w.

A reaction vessel was charged with dimethylamide and a stock aqueous NaOH solution (23% w/w) in the w/w ratio indicated in Table 6. The reaction vessel was sealed, and heated to 75° C. for 4 hours. The reaction mixture was subsequently analysed via Cation Ion Chromatography for formate and acetate formation. The molar amounts of formate and acetate measured to have been formed were taken to directly correspond to the molar amounts of DMF and DMAc that had undergone hydrolysis respectively.

TABLE 6

| Dimethyl-amide:NaOH sol<sup>n</sup> w/w | % Hydrolysed | | % w/v: Experimental Conversion Observed | | % w/v: Theoretical Total Conversion | |
|---|---|---|---|---|---|---|
| | DMF | DMAc | Formate | Acetate | Formate | Acetate |
| 50:50 | 27.1 | 0.6 | 7.70 | 0.02 | 28.4 | 3.47 |
| 40:60 | 77.5 | 8.8 | 17.14 | 0.24 | 22.12 | 2.72 |
| 35:65 | 96.5 | 9.4 | 19.2 | 0.23 | 19.90 | 2.45 |
| 10:90 | 99.7 | 97.2 | 5.76 | 0.69 | 5.78 | 0.71 |

Example 7

A two-neck round bottom flask, equipped with a reflux condenser and rubber septum, was charged with dimethylamide and the stock aqueous NaOH solution (23% w/w) in a ratio of 25:75 w/w, and the flask was heated to 90° C. in an oil bath. At the time intervals indicated in Table 7, the flask was removed from the oil bath, wiped free of oil, and weighed. A sample of the reaction mixture was then removed for analysis, and the flask reweighed to account for loss of volatiles and the aliquot removed. The reaction was then continued by replacing the flask in the oil bath. The aliquots of reaction mixture were analysed via Cation Ion Chromatography for formate and acetate formation. The molar amounts of formate and acetate measured to have been formed were taken to directly correspond to the molar amounts of DMF and DMAc that had undergone hydrolysis respectively. Values shown in Table 7 have been corrected for weight loss during reaction.

TABLE 7

| Time/h | % of DMF hydrolysed | % of DMAc hydrolysed | % w/v formate in solution (Theoretical Total Conversion = 14.19%) | % w/v acetate in solution (Theoretical Total Conversion = 1.72%) |
|---|---|---|---|---|
| 1 | 83.2 | 74.4 | 11.81 | 1.28 |
| 2 | 102.7 | 100.6 | 14.58 | 1.73 |
| 3 | 101.8 | 100.0 | 14.45 | 1.72 |
| 4 | 101.8 | 101.7 | 14.44 | 1.75 |
| 6 | 101.8 | 100.0 | 14.44 | 1.72 |

Example 8

The experiment of Example 7 was repeated, using a dimethylamide to NaOH solution (23% w/w) ratio of 30:70 w/w.

TABLE 8

| Time/h | % of DMF hydrolysed | % of DMAc hydrolysed | % w/v formate in solution (Theoretical Total Conversion = 17.08%) | % w/v acetate in solution (Theoretical Total Conversion = 2.08%) |
|---|---|---|---|---|
| 1 | 101.2 | 33.2 | 17.29 | 0.69 |
| 2 | 100.4 | 49.5 | 17.15 | 1.03 |
| 3 | 99.8 | 57.2 | 17.04 | 1.19 |
| 4 | 99.8 | 60.6 | 17.04 | 1.26 |
| 6 | 99.4 | 64.9 | 16.98 | 1.35 |

Data from Examples 7 and 8 pertaining to DMAc are expressed in FIG. 3.

Example 9

A vessel was charged with DMF and a pre-heated aqueous solution of NaOH to afford an aqueous reaction mixture comprising 0.070% w/w DMF and 0.077% w/w NaOH (molar ratio 1:2). The vessel was sealed and heated to 103° C. for the time indicated in Table 9. The reaction mixture was subsequently quenched with a 20% w/w aqueous solution of citric acid (citric acid solution:reaction mixture=1:15 w/w), and the reaction vessel plunged into ice water. The resultant mixture was analysed via Cation Ion Chromatography and Gas Chromatography to measure the amount of formate and DMF respectively present in the mixture.

TABLE 9

| Time/min | DMF/ppm | Formate/ppm |
|---|---|---|
| 0 | 693 | 0 |
| 5 | 565 | 61 |
| 10 | 465 | 126 |
| 20 | 300 | 203 |
| 30 | 255 | 246 |

Example 10

The experiment of Example 9 was repeated, using an aqueous reaction mixture comprising 0.070% w/w DMF and 0.192% w/w NaOH (molar ratio 1:5).

TABLE 10

| Time/min | DMF/ppm | Formate/ppm |
| --- | --- | --- |
| 0 | 693 | 0 |
| 5 | 256 | 234 |
| 10 | 194 | 268 |
| 20 | 86 | 346 |
| 30 | 43 | 403 |

Data from Examples 9 and 10 are expressed in FIG. 4.

Example 11

The experiment of Example 9 was repeated at room temperature, without pre-heating of the NaOH solution which was added at room temperature.

TABLE 11

| Time/h | DMF/ppm | Formate/ppm |
| --- | --- | --- |
| 0 | 700 | 0 |
| 6 | 550 | 20 |
| 30 | 387 | 150 |

Example 12

The experiment of Example 10 was repeated at room temperature, without pre-heating of the NaOH solution which was added at room temperature.

TABLE 12

| Time/h | DMF/ppm | Formate/ppm |
| --- | --- | --- |
| 0 | 700 | 0 |
| 6 | 416 | 74 |
| 30 | 173 | 294 |

Data from Examples 11 and 12 are expressed in FIG. 5.

Example 13

The experiment of Example 9 was repeated, using an aqueous reaction mixture comprising 0.210% w/w DMF and 0.230% w/w NaOH (molar ratio 1:2).

TABLE 13

| Time/min | DMF/ppm | Formate/ppm |
| --- | --- | --- |
| 0 | 1973 | 119 |
| 5 | 1257 | 556 |
| 10 | 917 | 782 |
| 20 | 640 | 960 |
| 30 | 338 | 1039 |

Figure 6:
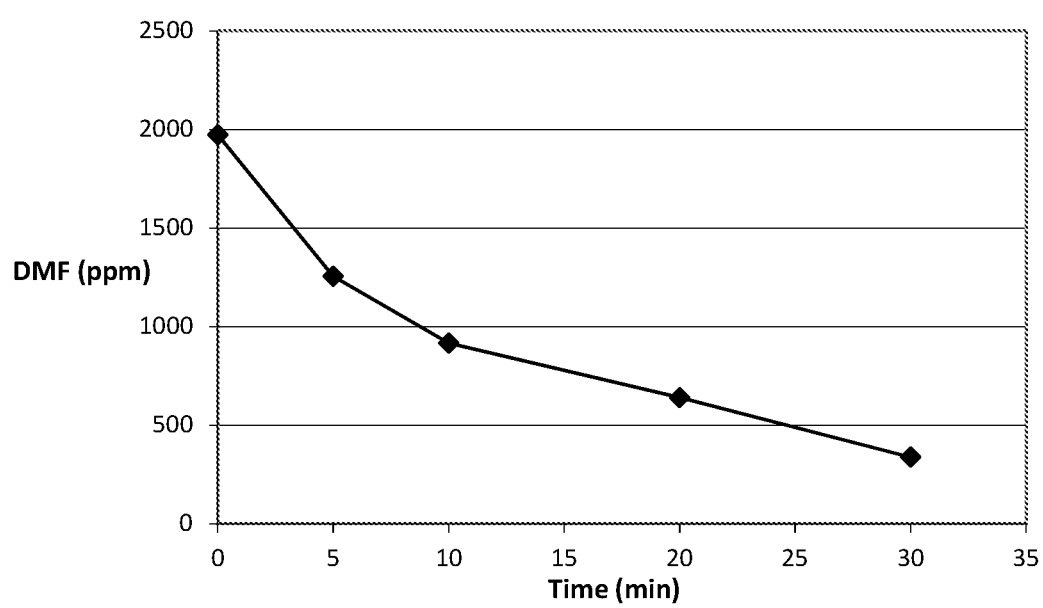
FIG. 6 is a graph which shows the rate of hydrolysis of DMF in an aqueous solution of DMF and NaOH at 103° C. (starting DMF concentration=2100 ppm).

Data from Example 13 are expressed in FIG. 6.

Example 14

A vessel was charged with DMF, DMA and pre-heated water to afford an aqueous reaction mixture comprising 0.070% w/w DMF and 3.000% w/w DMA. The vessel was sealed and heated to 103° C. for the time indicated in Table 14. The reaction mixture was subsequently quenched with a 20% w/w aqueous solution of citric acid (citric acid solution:reaction mixture=1:15 w/w), and the reaction vessel plunged into ice water. The resultant mixture was analysed via Cation Ion Chromatography and Gas Chromatography to measure the amount of formate and DMF respectively present in the mixture.

TABLE 14

| Time/min | DMF/ppm | Formate/ppm |
| --- | --- | --- |
| 0 | 700 | 0 |
| 5 | 604 | 81 |
| 10 | 503 | 131 |
| 20 | 362 | 222 |
| 30 | 275 | 269 |

Example 15

A vessel was charged with DMF, a pre-heated aqueous solution of NaOH and DMA to afford an aqueous reaction mixture comprising 0.070% w/w DMF, 0.077% w/w NaOH (molar ratio DMF:NaOH=1:2) and 3.000% w/w DMA. The vessel was sealed and heated to 103° C. for the time indicated in Table 15. The reaction mixture was subsequently quenched with a 20% w/w aqueous solution of citric acid (citric acid solution:reaction mixture=1:15 w/w), and the reaction vessel plunged into ice water. The resultant mixture was analysed via Cation Ion Chromatography and Gas Chromatography to measure the amount of formate and DMF respectively present in the mixture.

TABLE 15

| Time/min | DMF/ppm | Formate/ppm |
| --- | --- | --- |
| 0 | 693 | 0 |
| 5 | 471 | 100 |
| 10 | 361 | 193 |
| 20 | 230 | 290 |
| 30 | 148 | 365 |

Example 16

The experiment of Example 15 was repeated at 93° C.

TABLE 16

| Time/min | DMF/ppm | Formate/ppm |
| --- | --- | --- |
| 0 | 693 | 0 |
| 5 | 507 | 94 |
| 10 | 442 | 143 |
| 20 | 311 | 241 |
| 30 | 219 | 298 |

Example 17

The experiment of Example 15 was repeated, using an aqueous reaction mixture comprising 0.070% w/w DMF, 0.192% w/w NaOH (molar ratio DMF:NaOH=1:5) and 3.000% w/w DMA.

TABLE 17

| Time/min | DMF/ppm | Formate/ppm |
| --- | --- | --- |
| 0 | 693 | 0 |
| 5 | 446 | 179 |
| 10 | 288 | 283 |

TABLE 17-continued

| Time/min | DMF/ppm | Formate/ppm |
|---|---|---|
| 20 | 137 | 395 |
| 30 | 80 | 478 |

Figure 7:
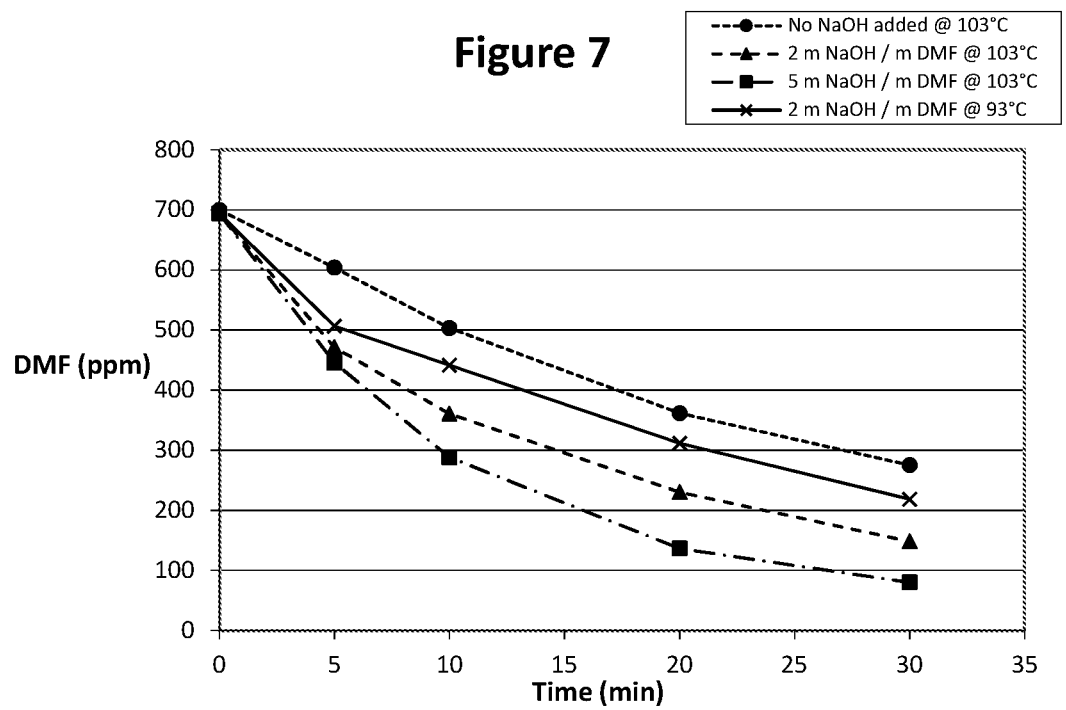
FIG. 7 is a graph which shows the rate of hydrolysis of DMF in an aqueous solution of DMF (starting concentration=700 ppm), DMA (dimethylamine, 3% w/w of reaction mixture) and NaOH (where indicated).

The data of Examples 14-17 are expressed in FIG. 7.

The invention claimed is:

1. A method of treating a waste stream, wherein the waste stream includes chlorinated carbohydrate and at least one of dimethyl formamide and dimethyl acetamide, wherein the method comprises:
 treating the waste stream with base at a pH of from 11 to 14, and at a temperature of from 200 to 330° F.,
 in order to achieve at least 90 percent dechlorination of said chlorinated carbohydrate wherein the dechlorination produces chloride, and at least one of a) at least 90 percent hydrolysis of said dimethyl formamide to give dimethylamine and b) at least 90 percent hydrolysis of said dimethyl acetamide to give dimethylamine.

2. A method according to claim 1, where the waste stream includes said dimethyl formamide and the treatment achieves hydrolysis of the dimethyl formamide to give dimethylamine.

3. A method according to claim 1, where the waste stream includes said dimethyl acetamide and the treatment achieves hydrolysis of the dimethyl acetamide to give dimethylamine.

4. A method according to claim 1, wherein the waste stream includes said dimethyl formamide and said dimethyl acetamide and the treatment achieves hydrolysis of the dimethyl formamide to give dimethylamine and hydrolysis of the dimethyl acetamide to give dimethylamine.

5. A method according to claim 1, wherein the waste stream is from a sucralose production process.

6. A method according to claim 1, wherein the waste stream includes sodium chloride.

7. A method according to claim 1 wherein the base is aqueous alkali solution.

8. A method according to claim 7, wherein the base is aqueous sodium hydroxide solution, potassium hydroxide solution, or aqueous ammonia.

9. A method according to claim 8, wherein the base is aqueous sodium hydroxide solution.

10. A method according to claim 9, wherein the base is from 10 to 50% w/w sodium hydroxide solution.

11. A method according to claim 10, wherein the base is from 23 to 32% w/w sodium hydroxide solution.

12. A method according to claim 1, wherein the pH of the treatment is from 11 to 13.5.

13. A method according to claim 12, wherein said pH is from 12 to 13.

14. A method according to claim 1, wherein the temperature of the treatment is from 210 to 280° F.

15. A method according to claim 1, wherein the pressure of the treatment is from 20 to 75 psig.

16. A method according to claim 1, wherein the waste stream is in aqueous medium, or in aqueous solution.

17. A method according to claim 2, wherein dimethylamine is recovered from the treatment.

18. A method according to claim 17, wherein the dimethylamine is recovered by distillation.

19. A method according to claim 18, wherein the dimethylamine is converted into dimethylformamide.

* * * * *